United States Patent

Vial et al.

[11] Patent Number: 5,834,491
[45] Date of Patent: Nov. 10, 1998

[54] BIS(2-AMINOPYRIDINE)S, PREPARATION METHOD THEREFOR AND USE THEREOF FOR CONTROLLING PARASITIC INFECTIONS

[75] Inventors: Henri Vial; Michèle Calas, both of Montpellier; Jean-Jacques Bourguignon, Hipsheim; Marie-Laure Ancelin, Saint-Jean-de-Cuculles; Louis Giral, Montpellier, all of France

[73] Assignee: Virbac, Carros, France

[21] Appl. No.: 809,919

[22] PCT Filed: Oct. 13, 1995

[86] PCT No.: PCT/FR95/01349

§ 371 Date: Jul. 2, 1997

§ 102(e) Date: Jul. 2, 1997

[87] PCT Pub. No.: WO96/11910

PCT Pub. Date: Apr. 25, 1996

[30] Foreign Application Priority Data

Oct. 14, 1994 [FR] France .................................. 94 12301

[51] Int. Cl.⁶ .......................... C07D 401/06; A61K 31/44
[52] U.S. Cl. ............................................. 514/332; 546/264
[58] Field of Search ................................ 546/264; 514/332

[56] References Cited

U.S. PATENT DOCUMENTS 4,206,215  6/1980  Bailey ...................................... 546/261

FOREIGN PATENT DOCUMENTS 0 494 754  7/1992  European Pat. Off. .

OTHER PUBLICATIONS

CA 98:4464, Inokuma et al., 1983.

*Primary Examiner*—Jane Fan
*Attorney, Agent, or Firm*—Bell Seltzer Intellectual Property Law Group of Alston & Bird LLP

[57] ABSTRACT

Substituted bis-2-aminopyridines of formula (1), wherein Q, R1,R2,R3,R4 are as defined in the specification. A method for preparing said compounds and the use thereof as a drug and in particular as active drugs for controlling parasiticc infections within red blood cells, e.g. malaria or babesiasis.

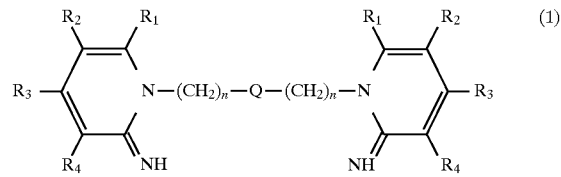

13 Claims, No Drawings

BIS(2-AMINOPYRIDINE)S, PREPARATION METHOD THEREFOR AND USE THEREOF FOR CONTROLLING PARASITIC INFECTIONS

The present invention relates to substituted bis(2-aminopyridine)s, to a process for preparing them and also to the applications of bis(2-aminopyridine)s, substituted or otherwise, as a medicinal product, in particular as medicinal products which are active against intraerythrocytic parasitoses such as malaria or babesiosis (or piroplasmosis).

Antimalarial and antibabesiosis activity is understood to mean the capacity to prevent the development of the parasite inside the erythrocyte and/or erythrocytic invasion, and to bring about the death of the parasites initially present.

Malaria or paludism remains the most important parasitic disease rampant in the intertropical regions. The World Health Organization estimates that there are some 350 million cases of malaria worldwide, 90% of them in Africa, causing the death of 1.5 to 2.7 million people per annum. From 1940 onwards, synthetic anti-folates such as Fansidar® (sulphonamide/pyrimethamine) and quinolines such as Nivaquine® (chloroquine) were employed to combat the disease. However, from the 1960s onwards, resistance appeared and necessitated the development of new active molecules, among them Lariam® (mefloquine) or Halfan® (halofantrine); nevertheless, these new molecules have also led to the emergence of new types of resistance, specific resistance but also cross-resistance. The emergence of chloroquine-resistant strains of *Plasmodium falciparum* in South-East Asia and in Latin America and the general expansion of these drug-resistance phenomena impose a limit on the effective treatment of malaria. In addition, the resistance to each of the new compounds, mefloquine and halofantrine, is also considerable and gives rise to a cross-resistance between these two substances.

Other substances such as artemisinine and its derivatives (artemether, artether, artesunate and dihydroartemisinine) are also used in China and in South-East Asia. However, these substances have the drawback of possessing a short half-life and low water-solubility.

Babesiosis, also known as piroplasmosis, is, like malaria, an intraerythrocytic parasitosis transmitted by tick bites, which affects many domestic and wild animal species and whose agent is a protozoan of the genus Babesia. There is thus a bovine babesiosis caused by *Babesia bovis, Babesia bigemina, Babesia major* and *Babesia divergens* which are responsible for considerable losses in cattle farming, in particular in developing countries. A canine babesiosis with *Babesia canis* and *Babesia gibsoni*, an equine babesiosis with *Babesia equi* and *cabalii* and even a rare but severe human babesiosis due to *Babesia divergens* and *Babesia microti* are also found.

Few substances are active against Babesia, and they are generally toxic (imidocarb and amicarbalide). Other products prove active in vitro without, however, giving good results in vivo, such as tubercidin, tetracycline or menoctone.

As early as 1984, McColm (Ann. Trop. Med. Parasitol., 78, (4), 345) stressed the increased resistance of Babesia towards classical antimicrobials such as tylosin, rifamycin and gramicidin D.

Consequently, it was the Applicant's objective to provide new products which are active against intraerythrocytic parasites.

The subject of the present invention is substituted bis(2-aminopyridine)s of general formula (I),

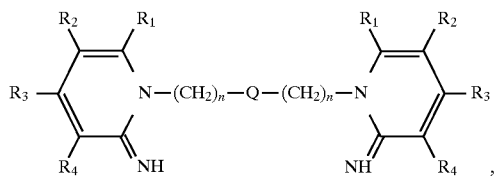

in which:
Q represents:
  a $C_6$–$C_{20}$ alkyl group,
  an optionally substituted aryl group, or
  a cycloalkyl group, and
  forms, between the 2 pyridine rings, a hydrocarbon linkage comprising in total from 6 to 34 carbon atoms,
n is a number between 0 and 7,
$R_1$, $R_2$, $R_3$ and $R_4$, which may be identical or different, represent:
  a hydrogen atom,
  an optionally substituted, linear or branched $C_1$–$C_6$ alkyl group,
  an aryl group optionally substituted with one or more halogen atoms or $C_1$–$C_6$ alkyl or $C_1$–$C_6$ alkoxy radicals,
  a benzyl group,
  a thienyl group, preferably a 2-thienyl,
  a furyl group, preferably a 2-furyl,
  a halogen atom,
  an alkoxy or benzyloxy group,
on condition that at least one of the radicals $R_1$, $R_2$, $R_3$ and $R_4$ is not a hydrogen atom when Q represents a linkage $(CH_2)_m$ with m between 6 and 20, as well as their addition salts.

Among the addition salts with acids, there may be mentioned those formed with inorganic acids such as hydrochloric, hydrobromic, nitric, sulphuric or phosphoric acids or organic acids such as acetic, propionic, maleic, benzoic, succinic, methanesulphonic, para-toluenesulphonic, fumaric and hydroxyethanesulphonic acids.

The expression $C_6$–$C_{20}$ alkyl denotes saturated or unsaturated, linear or branched alkyl groups.

The expression aryl denotes, for example, a phenyl radical optionally substituted with one or more fluorine, chlorine or bromine atoms or alkyl or alkoxy radicals.

The expression cycloalkyl can denote, for example, a cyclopropyl, cyclobutyl, cyclopentyl or cyclohexyl radical.

The expression $C_1$–$C_6$ alkyl denotes saturated or unsaturated, linear or branched alkyl groups such as, for example, methyl, ethyl, propyl, butyl, isopropyl, isobutyl, sec-butyl, tert-butyl, pentyl, hexyl, trifluoromethyl, vinyl and allyl groups.

The expression alkoxy denotes $C_1$–$C_6$ alkoxy groups such as methoxy, ethoxy, propoxy and butoxy groups.

The expression halogen denotes a fluorine, chlorine or bromine atom.

Although other bis(aminopyridine)s have been described, namely bis(4-aminopyridine)s (U.S. Pat. No. 4,206,215 and J. Med. Chem. 1984, 27, 1457–1464) which display activity in the treatment of dental plaque, or bis(2-aminopyridine)s unsubstituted on the pyridine rings having iodination-catalyst activity (INOKUMA, Yakagaku, 1982, 31, (8), 515–19), the Applicant found, surprisingly, that both unsubstituted bis(2-aminopyridine)s and bis(2-aminopyridine)s bearing at least one substitution, as are defined above, possess antiparasitic activity and in particular an exceedingly advantageous and unexpected antimalarial and antibabesiosis activity; the substituted bis(2-aminopyridine)s display especially advantageous activity.

In effect, the products of formula I as defined above, as well as the products of formula I in which $R_1$, $R_2$, $R_3$ and $R_4$ represent hydrogen atoms, as well as their addition salts with acids, display advantageous pharmacological properties. They are endowed, in particular, with very good activity against intraerythrocytic parasitoses.

Unexpectedly, these products block the erythrocytic proliferation of the parasite. In effect, these products interfere in the metabolism of the parasite by blocking the transport of choline, an essential precursor of the phosphatidylcholines which are constituents of the cell membranes and necessary for the proliferation of the parasites, which proliferation is accompanied by a considerable de novo synthesis of the phospholipids which are necessary for the biogenesis of the cell membranes.

The compounds according to the invention display very strong activity in vitro against strains or isolates which are chemoresistant in a variety of ways. The activity is exerted mainly against the mature erythrocytic stages, the most intense phase of phospholipid synthesis. In particular, in murine systems infected with *Plasmodium chabaudi* or *Plasmodium petteri*, the compounds according to the invention eradicate the parasitaemia completely.

The subject of the invention is, more especially, the products defined above, characterized in that, in the formula (I), $R_1$, $R_2$, $R_3$ or $R_4$ represents a methyl, chloro or phenyl group at positions 3, 4 and/or 5, and Q represents a $C_1$–$C_{20}$ alkyl group, the hydrocarbon linkage between the two pyridine rings constituting a dodecane, a hexadecane, an octane or a decane.

According to the invention, the products of formula I above and their salts may be prepared by a process which is characterized in that a derivative of formula (II) Hal—$(CH_2)_n$—Q—$(CH_2)_n$—Hal, in which Hal represents a halogen atom and n and Q have the general meaning stated above, is reacted in solution with a compound of formula (III):

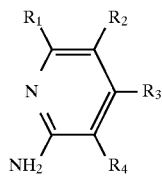

in which $R_1$, $R_2$, $R_3$ and $R_4$ have the meaning given above, to obtain the product of general formula (I) in the state of the corresponding dihalide which, if desired, is alkalinized and converted to another salt of an acid.

Under the preferred conditions of implementation of the invention, the process described above is carried out in the following manner:

The reaction of a compound of formula II and a compound of formula III, present in a 1:2 ratio, the compound of formula II preferably being in slight excess, to bring about the total conversion of the aminopyridines (derivative of formula III), is carried out:
  in the presence of a solvent or mixture of solvents which is/are inert towards the reactants employed, the solvent being chosen from acetonitrile, aromatic hydrocarbons (toluene, xylenes), aliphatic ketones such as propanone, butanone and 3-methyl-2-butanone, alcohols (methanol, ethanol, propanol, butanol), dimethylformamide and common ethers, for example dioxane, monoglyme and diglyme,
  at room temperature or in the heated state (boiling point of the solvent, in particular),
  for a few hours to several days.

The reaction may also be conducted without adding a solvent, provided one of the reactants is liquid at the reaction temperature and thus dissolves the other reactant. An advantage of the present process is that the dihydrohalide, in general hydrobromide or hydrochloride, of the desired bis (aminopyridine)s is obtained directly at the end of the reaction, and crystallizes directly in the pure state in the solvent.

It is possible, however, to obtain the corresponding bases by displacing the hydrohalide ion, for example with an ion exchange resin or by precipitating a silver halide, and converting them to another salt of a pharmaceutically acceptable inorganic or organic acid.

The collective products of formula (I) and their salts of acids which are acceptable from a pharmaceutical standpoint may be administered to man or animals as a medicinal product, in the form of pharmaceutical compositions comprising as active constituent an effective dose of at least one product of formula (I) or of an addition salt with an acid of such a compound, with, in addition, excipients and additives taken from those which are normally used in pharmacy.

These compositions may be administered orally, parenterally or rectally, in particular in the form of tablets, dragees, capsules, solutions, syrups, emulsions or suspensions, pharmaceutical dosage forms capable of modulating the release of the active substance.

Such compositions are generally administered at a dose of 0.5 to 50 mg/kg.

Besides the foregoing arrangements, the invention also comprises other arrangements which will become apparent from the description which follows, which relates to examples of embodiment of the process which is the subject of the present invention.

It should be clearly understood, however, that these examples are given only by way of illustration of the subject of the invention and in no way constitute a limitation of the latter.

All the derivatives synthesized were subjected to an elemental analysis, with a maximum tolerance of 0.3% in the results obtained relative to the results calculated.

Proton nuclear magnetic resonance spectra were recorded in solution in $CDCl_3$+TMS or in DMSO-$d_6$ on a Brucker WP 200 instrument. The most characteristic chemical shifts are, where appropriate, shown in these examples. Except where specifically stated, all the products were isolated in the state of hydrobromides.

EXAMPLE 1

1,1'-(1,12-dodecanediyl)bis(4-methyl-2(1H)-pyridinimine) dihydrobromide 0.1 mol of commercial 1,12-dibromododecane is dissolved in 500 milliliters of methyl ethyl ketone, 0.15 mol of 4-methyl-2-aminopyridine dissolved in methyl ethyl ketone is introduced under argon and the mixture is left stirring at the refluxing temperature until completion of the reaction, which may be monitored by thin-layer chromatography and most generally takes 48 hours. After the precipitate has been filtered off and rinsed, the crude product is obtained in the form of its hydrobromide. The product may be recrystallized in a 9:1 isopropanol/methanol mixture. Beautiful white crystals, m.p. 206° C., are thereby obtained in a yield on the pure product of 66%.

As a variant, the product is prepared as follows:

0.36 g (3.3 mmol) of 4-methyl-2-aminopyridine is dissolved in 5 ml of n-BuOH and refluxed under argon for 48 hours in the presence of 0.50 g (1.52 mmol) of 1,12-dibromododecane. After cooling of the reaction medium, the product crystallizes.

It is recovered by filtration, rinsed with a little isopropanol and then ether and dried.

0.30 g of salt is obtained (47% yield).

Empirical formula: $C_{24}H_{40}N_4Br_2$; molecular weight: 436.28; $^1$H NMR (200 MHz, DMSO-$d_6$): 8.27 (broad s, 4H, 2x—$NH_2$, exchangeable; 7.98–7.96 (part A of an AB system, 2H, 12x$H_6$); 6.81 (m, 4H, 2x($H_3$+$H_5$)); 4.08–4.05 (m, 4H, 2x>N—$CH_2$—); 2.31 (s, 6H, 2x—$CH_3$); 1.23–1.63 (m, 20H, 10x—$CH_2$—).

EXAMPLE 2

1,1'-(1,12-dodecanediyl)bis(3-methyl-2(1H)-pyridinimine) dihydrobromide 0.1 mol of commercial 1,12-dibromododecane is dissolved in 500 milliliters of methyl ethyl ketone, 0.15 mol of 3-methyl-2-aminopyridine dissolved in methyl ethyl ketone is introduced under argon and the mixture is left stirring at the refluxing temperature until completion of the reaction, which may be monitored by thin-layer chromatography and most generally takes 48 hours. After the precipitate has been filtered off and rinsed, the crude product is obtained in the form of its hydrobromide. The product may be recrystallized in a 9:1 isopropanol/methanol mixture. Beautiful white crystals, m.p. 229° C., are thereby obtained in a yield on the pure product of 38%.

Empirical formula: $C_{24}H_{40}N_4Br_2$; molecular weight: 544.42; $^1$H NMR (200 MHz, DMSO-$d_6$): 8.08 (broad s, 4H, 2x—$NH_2$ exchangeable); 8.00 (part A of an AB system, 2H, 2x$H_6$); 7.77 (m, 2H, 2x$H_5$); 6.88–6.85 (part B of an AB system, 2H, 2x$H_4$); 4.21 (m, 4H, 2x>N—$CH_2$—); 2.22 (s, 6H, 2x—$CH_3$); 1.23–1.63 (m, 20H, 10x—$CH_2$—).

EXAMPLE 3

1,1'-(1,12-dodecanediyl)bis(5-methyl-2(1H)-pyridinimine) dihydrobromide 0.1 mol of commercial 1,12-dibromododecane is dissolved in 500 milliliters of methyl ethyl ketone, 0.15 mol of 5-methyl-2-aminopyridine dissolved in methyl ethyl ketone is introduced under argon and the mixture is left stirring at the refluxing temperature until completion of the reaction, which may be monitored by thin-layer chromatography. After the precipitate has been filtered off and rinsed, the crude product is obtained in the form of its hydrobromide. The product may be recrystallized in a 9:1 isopropanol/methanol mixture. The derivative of the title is obtained in a 40% yield, having an m.p. of 221° C.

Empirical formula: $C_{24}H_{40}N_4Br_2$; molecular weight: 544.42; $^1$H NMR (200 MHz, DMSO-$d_6$): 8.08 (broad s, 4H, 2x—$NH_2$ exchangeable); 8.00 (m, 2H, 2x$H_6$); 7.70 (part A of an AB system, 2H, 2x$H_3$); 6.80 (part B of an AB system, 2H, 2x$H_4$); 4.20 (m, 4H, 2x>N—$CH_2$—); 1.2–1.63 (m, 20H, 10x—$CH_2$—).

EXAMPLE 4

1,1'-(1,12-dodecanediyl)bis(6-methyl-2(1H)-pyridinimine) dihydrobromide

The reaction is performed under the conditions described above, starting from 6-methyl-2-aminopyridine. The product is purified by recrystallization in isopropanol. The derivative of the title, m.p. 205° C., is obtained in a 23% yield.

EXAMPLE 5

1,1'-(1,12-dodecanediyl)bis(5-phenyl-2(1H)-pyridinimine) dihydrobromide

The procedure is as before, with dibromododecane and 2-amino-5-phenylpyridine. The product obtained is purified by recrystallization in methanol. Its m.p.=185° C.

EXAMPLE 6

1,1'-(1,12-dodecanediyl)bis(3-phenylmethoxy-2(1H)-pyridinimine) dihydrobromide

The procedure is as above, with dibromododecane and 2-amino-3-(phenylmethoxy)pyridine, which was synthesized by the method described by Rydzkowski R. in Tetrahedron Letters 26 (1985) 2571–1574.

EXAMPLE 7

1,1'-(1,12-dodecanediyl)bis(4-(4-methyl-phenyl)-2(1H)-pyridinimine) dihydrobromide The procedure is as above, with dibromododecane and 2-amino-4-para-tolylpyridine, which is synthesized according to Chambron J.Cl. Strasbourg Tetrah. 1987 43 (5) 895/905. The product obtained is purified in the base state on a silica column with a benzene/ethyl acetate mixture. It is reconverted to the hydrobromide with a mixture of ether and an isopropanol solution of hydrogen bromide. It can then be recrystallized.

EXAMPLE 8

1,1'-(1,12-dodecanediyl)bis(3-n-butyl-2(1H)-pyridinimine) dihydrobromide

2-Amino-3-n-butylpyridine is prepared according to Gassman J. Amer. Chem. Soc. 95 (1973).4453, and condensed as above with the corresponding dibromododecane. The desired product, m.p. 192° C., is obtained.

EXAMPLE 9

1,1'-(1,12-dodecanediyl)bis(5-chloro-2(1H)-pyridinimine) dihydrobromide

The reaction is performed under the conditions of Example 1, with 2-amino-5-chloropyridine in methyl ethyl ketone. After recrystallizations in a 9:1 isopropanol/methanol mixture, the derivative of the title, m.p. 239° C., is obtained in an 18% yield.

This product has the following empirical formula: $C_{22}H_{34}N_4Br_2Cl_2$.

Molecular weight: 585.26.

$^1$H NMR (200 MHz, DMSO-$d_6$): 8.67 (broad s, 4H, 2x—$NH_2$+exchangeable); 8.46 (m, 2H, 2x$H_6$); 7.99 (part A of an AB system, 2H, 2x$H_3$); 7.05 (part B of an AB system, 2H, 2x$H_4$); 4.09 (m, 4H, 2x>N—$CH_2$—); 1.2–1.66 (m, 20H, 10x—$CH_2$—).

EXAMPLE 10

1,1'-(1,12-dodecanediyl)bis(4-bromo-2(1H)-pyridinimine) dihydrobromide

The procedure is as above, using 2-amino-4-bromopyridine (according to Larsen, Scott WO 93/25553) and the desired derivative, m.p. 230° C., is obtained.

EXAMPLE 11

1,1'-(1,12-dodecanediyl)bis(3-chloro-5-trifluoromethyl-2(1H)-pyridinimine) dihydrobromide

2-Amino-3-chloro-5-trifluoromethylpyridine, synthesized according to Haga Takahiro Heterocycles, 22 (1984) 1, 117–124, is used. By treatment according to the previous process, the derivative, m.p. 185° C., is isolated.

EXAMPLE 12

1,1'-(1,8-octanediyl)bis(5-methyl-2(1H)-pyridinimine) dihydrobromide

0.1 mol of commercial 1,8-dibromooctane is dissolved in 500 milliliters of methyl ethyl ketone, 0.15 mol of 5-methyl-2-aminopyridine dissolved in methyl ethyl ketone is introduced under argon and the mixture is left stirring at the refluxing temperature until completion of the reaction, which may be monitored by thin-layer chromatography and most generally takes 48 hours. After the precipitate has been filtered off and rinsed, the crude product is obtained in the form of its hydrobromide. The product may be recrystallized in a 9:1 isopropanol/methanol mixture. The derivative of the title is obtained in a 40% yield, having an m.p. of 241° C.

EXAMPLE 13

1,1'-(1,8-octanediyl)bis(4-methyl-2(1H)-pyridinimine

0.1 mol of commercial 1,8-dibromooctane is dissolved in 500 milliliters of methyl ethyl ketone, 0.15 mol of 4-methyl-2-aminopyridine dissolved in methyl ethyl ketone is introduced under argon and the mixture is left stirring at the refluxing temperature until completion of the reaction, which may be monitored by TLC. After the precipitate has been filtered off and rinsed, the crude product is obtained in the form of its hydrobromide. The product may be recrystallized in a 9:1 isopropanol/methanol mixture. Beautiful white crystals, m.p. 248° C., are thereby obtained in a yield on the pure product of 47%.

As a variant, this product is prepared as follows:

2 g of 2-amino-4-methylpyridine (18.5 mmol, 3 equivalents) and 6.16 mmol (1.7 ml) of 1,8-dibromooctane in 50 ml of butanone are introduced into a 100-ml ground-necked Erlenmeyer equipped with a condenser denser and a magnetic stirrer. The mixture is heated to reflux for 36 hours and then left at 4° C. overnight. The precipitate is filtered off and recrystallized in a methanol/isopropanol/ether mixture (48 h at 4° C.). Beautiful white crystals, m.p. between 247° and 250° C., are thereby obtained in a yield on the pure product of 52%.

$^1$H NMR in DMSO-D$_6$ (δ in ppm): 1.25 (m, 8H); 1.65 (m, 4H); 2.3 (s, 6H); 4.1 (t, 4H); 6.85 (m, 4H); 8.00 (d, 2H); 8.45 (s, 4H).

EXAMPLE 14

1,1'-(1,6-hexanediyl)bis(4-methyl-2(1H)-pyridinimine) dihydrobromide

The reaction is performed under the conditions described above, with 1,6-dibromohexane. After recrystallization in isopropanol, the derivative of the title, m.p. 253° C., is obtained.

EXAMPLE 15

1,1'-(1,16-hexadecanediyl)bis(4-methyl-2(1H)-pyridinimine dihydrobromide

The reaction is performed under the usual conditions, with 1,16-dibromohexadecane, and, after recrystallization in an isopropanol/methanol mixture, the derivative of the title, m.p. 167°–170° C., is obtained.

As a variant, this product is prepared as follows:

2.11 g of 2-amino-4-methylpyridine (3 equivalents) and 249 mg (0.65 mmol) of 1,16-dibromododecane in 5 ml of butanone are introduced into a 100-ml ground-necked Erlenmeyer equipped with a condenser and a magnetic stirrer. The mixture is heated to reflux for 36 hours; the solvent is evaporated off, and isopropanol is added, followed by ether, until the mixture becomes cloudy. The solution is left at 40° for 2 days.

The precipitate obtained is filtered off and dried in a desiccator. A product is thereby obtained in a 39% yield.

$^1$H NMR in DMSO-D$_6$ (δ in ppm): 1.2 (m, 24H); 1.65 (m, 4H) ; 2.3 (s, 6H) ; 4.1 (t, 4H); 6.8 (m, 4H); 7.95 (d, 2H); 8.3 (s, 4H).

EXAMPLE 16

1,1'-(1,16-hexadecanediyl)bis(4-ethyl-2(1H)-pyridinimine) dihydrobromide

Starting from 4-ethyl-2-aminopyridine described by Hansch and 1,16-dibromohexadecane, the derivative of the title, m.p. 105°/110° C., is obtained.

Using the method of Example 1 and starting from the various dimethyl-2-aminopyridines synthesized according to the literature (Dornow, Rohe, Chem. Ber., 93, 1960, 1093/1097; Wentrup, Mayov, J. Amer. Chem. Soc., 97, 1975, 7468/7477; Rao Venkateswarlu, J. Heterocycl. Chem., 12, 1975, 731/732), the 1,1'-(1,12-dodecanediyl)bis (dimethyl-substituted 2(1H)pyridinimine)s are obtained in the state of dihydrobromides, as follows:

EXAMPLE 17

1,1'-(1,12-dodecanediyl)bis(3,4-dimethyl-2(1H)-pyridinimine)

EXAMPLE 18

1,1'-(1,12-dodecanediyl)bis(3,5-dimethyl-2(1H)-pyridinimine)

EXAMPLE 19

1,1'-(1,12-dodecanediyl)bis(3,6-dimethyl-2(1H)-pyridinimine)

EXAMPLE 20

1,1'-(1,12-dodecanediyl)bis(4,5-dimethyl-2(1H)-pyridinimine)

EXAMPLE 21

1,1'-(1,12-dodecanediyl)bis(4,6-dimethyl-2(1H)-pyridinimine)

EXAMPLE 22

1,1'-(1,12-dodecanediyl)bis(5,6-dimethyl-2(1H)-pyridinimine)

Using the same method and starting from the ethyl-2-aminopyridines synthesized according to the processes of the literature, such as Robison, J. Amer. Chem. Soc., 79, 1957, 2573/2576; Hansch, J. Org. Chem. 23, 1958, 1924; Childress, J. Org. Chem., 23, 1958, 67; Yakhontov, Chem.

Heterocycl. Compd., 3, 1967, 829/830, the 1,1'-(1,12-dodecanediyl)bis(alkyl-substituted 2(1H)-pyridinimine)s are obtained.

EXAMPLE 23

1,1'-(1,12-dodecanediyl)bis(3-ethyl-2(1H)-pyridinimine)

EXAMPLE 24

1,1'-(1,12-dodecanediyl)bis(4-ethyl-2(1H)-pyridinimine)

EXAMPLE 25

1,1'-(1,12-dodecanediyl)bis(5-ethyl-2(1H)-pyridinimine)

EXAMPLE 26

1,1'-(1,12-dodecanediyl)bis(6-ethyl-2(1H)-pyridinimine)

PHARMACOLOGICAL TESTS

ANTIMALARIAL ACTIVITY IN VITRO TOWARDS PLASMODIUM FALCIPARUM

Evaluation of the antimalarial activity in vitro is carried out according to the method of DESJARDINS, CANFIELD, HATNES and CHULAY (Antimicrob. Agents Chemother., 1979, 16, 710–718). A compound according to the invention is brought into contact for approximately 48 hours with human erythrocytes infected with Plasmodium falciparum. When a radioactive nucleic acid precursor, hypoxanthine, is added to the preparation, only erythrocytes infected with Plasmodium and not affected by the said compound incorporate this precursor. The ability or inability to incorporate the precursor hence reflects the viability of the malaria-infected cells. The results are presented in Table I below, in the form of an $IC_{50}$ (or $ED_{50}$) (concentration of compound capable of inhibiting in vitro the growth of the parasites by 50%).

The derivatives according to the above examples are tested at three concentrations, 100, 33 and 10 nanomolar.

Verification of the mechanism of action is carried out on the various derivatives according to the invention by studying the specific interference with phospholipid biosynthesis and measuring the biosynthesis of the different biomolecules, nucleic acids, proteins and phospholipids, on the basis of the incorporation of radiolabelled precursors, [$^3$H]hypoxanthine (see above), [$^3$H]isoleucine and [$^3$H]choline. The specificity in the precise realm of phospholipid metabolism is determined by comparison with the effect on the incorporation of [$^3$H]ethanolamine into phosphatidylethanolamine (Ancelin M. L., Vialettes F. and Vial H. J., 1991, Anal. Biochem., 199, 203–209). Under these conditions and among all of the derivatives described above, the compound of Example 1 is the one which proved to have the best specificity of action towards the biosynthesis of phosphatidylcholine, relative to the biosyntheses of the other macromolecules (nucleic acids, proteins, other phospholipids).

ANTIMALARIAL ACTIVITY AND TOXICITY IN VIVO

This activity is measured according to the test described by PETERS W. (Chemotherapy and Drug resistance in Malaria, 1970). A compound according to the invention is administered for 4 consecutive days to mice infected beforehand with malaria using Plasmodium vinckei, petteri or chabaudi.

The said compound is dissolved in 0.9% aqueous NaCl solution or, where appropriate, in 10% aqueous gum arabic solution. The preparations are thus administered intraperitoneally or subcutaneously to male Swiss mice of average weight 30 to 40 g which have been infected beforehand intravenously with Plasmodium petterei or P. chabaudi ($10^6$ infected cells). The compound is administered twice daily for 4 consecutive days, the first injection being performed 2 hours after infestation, and the second 10 hours after. The parasitaemia is determined by means of a smear on the day following the end of the treatment.

The results are collated in Table II, in the form of an $ED_{50}$ (dose of compound administered in vivo capable of a 50% inhibition of the growth of the parasites). This Table II also shows the toxicity measured according to the same method, the animals having received, under the conditions of administration used for the above tests, 2 injections daily for four days (semi-chronic toxicity); the results are expressed in the form of an $LD_{50}$ (dose of compound bringing about the death of 50% of the animals).

ANTIBABESIA ACTIVITY IN VITRO

The screening method used for the antimalaria series and based on the incorporation of [$^3$H]hypoxanthine by the parasite can be used to test the antimetabolite activity of such compounds on Babesia bovis. A close relationship is found between the degree of incorporation of [$^3$H]hypoxanthine in a standard measurement and the percentage of cells parasitized, determined by microscopic examination. The concentrations of the compounds causing a 50% inhibition of the incorporation of [$^3$H]hypoxanthine ($ID_{50}$) are summarized in Table I below.

TABLE I

| Compound | Plasmodium $IC_{50}$ in vitro resp. 100 nM | Plasmodium $IC_{50}$ in vitro resp. at 33 nM | Plasmodium $IC_{50}$ in vitro resp. at 10 nM | Plasmodium $IC_{50}$ in vitro resp. <10 nM | Babesia bovis - activity at 10 mM |
|---|---|---|---|---|---|
| Example 1 | + | + | + | + | + |
| Example 2 | + | + | + | + | + |
| Example 3 | + | + | + | + | + |
| Example 4 | + | + | + | − | + |
| Example 5 | + | + | + | − | |
| Example 6 | + | + | + | − | + |
| Example 7 | + | + | + | − | − |

TABLE I-continued

| Compound | Plasmodium IC$_{50}$ in vitro resp. 100 nM | Plasmodium IC$_{50}$ in vitro resp. at 33 nM | Plasmodium IC$_{50}$ in vitro resp. at 10 nM | Plasmodium IC$_{50}$ in vitro resp. <10 nM | *Babesia bovis* - activity at 10 mM |
|---|---|---|---|---|---|
| Example 8  | + | + | + | − | + |
| Example 9  | + | + | + | − | − |
| Example 10 | + | + | + | − | + |
| Example 11 | + | + | + | − | + |
| Example 12 | + | − | − | − | − |
| Example 13 | + | + | − | − | − |
| Example 14 | + | − | − | − | − |
| Example 15 | + | + | − | − | + |
| Example 16 | + | − | − | − | + |
| Example 17 | + | + | + | − | + |
| Example 18 | + | + | + | − | + |
| Example 19 | + | + | + | + | + |
| Example 20 | + | + | − | − | + |
| Example 21 | + | + | + | + | + |
| Example 22 | + | + | + | − | − |
| Example 23 | + | − | − | − | − |
| Example 24 | − | − | − | − | − |
| Example 25 | + | + | − | − | − |
| Example 26 | + | + | + | − | − |

TABLE II

| Compound | Activity in vitro IC$_{50}$ nanomolar | Activity in vivo ED$_{50}$ mg/kg I.P. | Toxicity LD$_{50}$ mg/kg I.P. | Toxicity LD$_{50}$ mg/kg P.O. |
|---|---|---|---|---|
| Example 1  | 0.5 | 1.2 | 30  | 365  |
| Example 2  | 1.8 | 3   | 20  | >500 |
| Example 3  | 0.5 | 3   | 6.5 | >300 |
| Example 9  | 1.4 | 4   | 10  | >200 |
| Example 23 | 7.2 | >5  | 23  | >400 |
| Example 25 | 3.8 | >5  | 7.5 | >200 |

As is apparent from the foregoing, the invention is in no way limited to those of its embodiments and modes of implementation and application which have just been described more explicitly; it embraces, on the contrary, all the variants which may occur to the practitioner in the field, without departing from the scope or compass of the present invention.

We claim:

1. A bis(2-aminopyridine) of formula (I) and an addition salt thereof, wherein the formula (I) is represented by

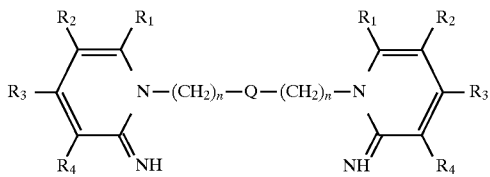

in which:

Q represents:
(a) a $C_6$–$C_{20}$ alkyl group,
(b) an optionally substituted aryl group, or
(c) a cycloalkyl group, and
forms, between the 2 pyridine rings and with the groups $(CH_2)_n$, a hydrocarbon linkage constituted in total of from 6 to 34 carbon atoms;

n is a number between 0 and 7;

$R_1$, $R_2$, $R_3$, and $R_4$, which may be identical or different, represent:

(1) a hydrogen atom,
(2) an optionally substituted, linear or branched $C_1$–$C_6$ alkyl group,
(3) an aryl group optionally substituted with one or more halogen atoms or $C_1$–$C_6$ alkyl or $C_1$–$C_6$ alkoxy radicals,
(4) a benzyl group,
(5) a thienyl group,
(6) a furyl group,
(7) a halogen atom, or
(8) an alkoxy or benzyloxy group,
and at least one of above (1) to (8) being not a hydrogen atom.

2. A bis(2-aminopyridine) of formula (I) and an addition salt thereof, said formula (I) being represented by

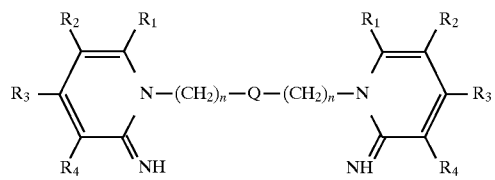

in which:

Q represents:
(a) a $C_6$–$C_{20}$ alkyl group selected from the group consisting of unsaturated linear alkyl groups, saturated branched alkyl groups, and unsaturated branched alkyl groups,
(b) an optionally substituted aryl group, or
(c) a cycloalkyl group, and
forms, between the 2 pyridine rings and with the groups $(CH_2)_n$ a hydrocarbon linkage constituted in total of from 6 to 34 carbon atoms;

n is a number between 0 and 7;

$R_1$, $R_2$, $R_3$ and $R_4$, which may be identical or different, represent:

(1) a hydrogen atom,
(2) an optionally substituted, linear or branched $C_1$–$C_6$ alkyl group,
(3) an aryl group optionally substituted with one or more halogen atoms or $C_1$–$C_6$ alkyl or $C_1$–$C_6$ alkoxy radicals, (4) a benzyl group,
(5) a thienyl group,
(6) a furyl group,
(7) a halogen atom, or
(8) an alkoxy or benzyloxy group.

3. A bis(2-aminopyridine), according to claim 1, wherein $R_1$, $R_2$, $R_3$, or $R_4$ represents
(a) a methyl group,
(b) a chloro group, or
(c) a phenyl group being optionally substituted at one or more of the positions 3, 4 and 5; and Q represents a $C_6$–$C_{20}$ alkyl group, the hydrocarbon linkage between the two pyridine rings comprising of a dodecane, a hexadecane, an octane or a decane.

4. A process for making a bis(2-aminopyridine) of formula (I) and an addition salt thereof, wherein formula (I) is represented by

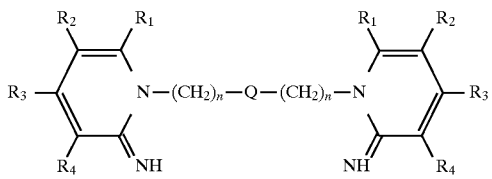

in which,
Q represents:
(a) a $C_6$–$C_{20}$ alkyl group,
(b) an optionally substituted aryl group, or
(c) a cycloalkyl group, and
forms, between the 2 pyridine rings and with the groups $(CH_2)_n$, a hydrocarbon linkage constituted in total of from 6 to 34 carbon atoms;
n is a number between 0 and 7;
$R_1$, $R_2$, $R_3$, and $R_4$ which may be identical or different, represent:
(1) a hydrogen atom,
(2) an optionally substituted, linear or branched $C_1$–$C_6$ alkyl group,
(3) an aryl group optionally substituted with one or more halogen atoms or $C_1$–$C_6$ alkyl or $C_1$–$C_6$ alkoxy radicals,
(4) a benzyl group,
(5) a thienyl group,
(6) a furyl group,
(7) a halogen atom, or
(8) an alkoxy or benzyloxy group,
and at least one of above (1) to (8) being not a hydrogen atom, comprising reacting a derivative of a compound of formula (II) with a compound of formula (III) to obtain the product of formula (I) in the state of the corresponding dihalide which, if desired, is alkalinized and converted to another salt of an acid, wherein,
formula (II) is represented by Hal—$(CH_2)_n$—Q—$(CH_2)_n$—Hal,
in which:
Hal representing a halogen atom;
n is a number between 0 and 7;
Q represents:
(a) a $C_6$–$C_{20}$ alkyl group,
(b) an optionally substituted aryl group, or
(c) a cycloalkyl group, and
forms, between the 2 pyridine rings and with the groups $(CH_2)_n$, a hydrocarbon linkage constituted in total of from 6 to 34 carbon atoms; and formula (III) is represented by

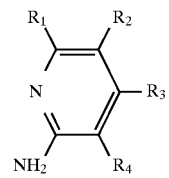

in which $R_1$, $R_2$, $R_3$, and $R_4$, which may be identical or different, represent:
(1) a hydrogen atom,
(2) an optionally substituted, linear or branched $C_1$–$C_6$ alkyl group,
(3) an aryl group optionally substituted with one or more halogen atoms or $C_1$–$C_6$ alkyl or $C_1$–$C_6$ alkoxy radicals,
(4) a benzyl group,
(5) a thienyl group,
(6) a furyl group,
(7) a halogen atom, or
(8) an alkoxy or benzyloxy group,
and at least one of above (1) to (8) being not a hydrogen atom.

5. A process for making a bis(2-aminopyridine) of formula (I) and an addition salt thereof, wherein formula (I) is represented by

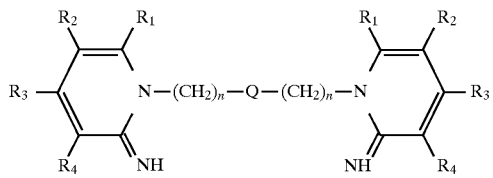

in which,
Q represents:
(a) a $C_6$–$C_{20}$ alkyl group selected from the group consisting of unsaturated linear alkyl groups, saturated branched alkyl groups, and unsaturated branched alkyl groups,
(b) an optionally substituted aryl group, or
(c) a cycloalkyl group, and
forms, between the 2 pyridine rings and with the groups $(CH_2)_n$ a hydrocarbon linkage constituted in total of from 6 to 34 carbon atoms;
n is a number between 0 and 7;
$R_1$, $R_2$, $R_3$ and $R_4$, which may be identical or different, represent:
(1) a hydrogen atom,
(2) an optionally substituted, linear or branched $C_1$–$C_6$ alkyl group,
(3) an aryl group optionally substituted with one or more halogen atoms or $C_1$–$C_6$ alkyl or $C_1$–$C_6$ alkoxy radicals,
(4) a benzyl group,
(5) a thienyl group,
(6) a furyl group,
(7) a halogen atom, or
(8) an alkoxy or benzyloxy group, comprising reacting a derivative of a compound of formula (II) with a compound of formula (III) to obtain the product of formula (I) in the state of the corresponding dihalide which, if desired, is alkalinized and converted to another salt of an acid, wherein, formula (II) is represented by Hal—$(CH_2)_n$—Q—$(CH_2)_n$—Hal,
in which:
Hal representing a halogen atom;
n is a number between 0 and 7;
Q has the meaning given above in formula (I); and
formula (III) is represented by

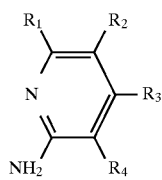

in which $R_1$, $R_2$, $R_3$ and $R_4$ have the meaning given above in formula (I).

6. A process according to claim 4, wherein the compound of formula (II) and the compound of formula (III) are present in a 1:2 ratio, the compound of formula II preferably being in slight excess.

7. A process according to claim 5, wherein the compound of formula (II) and the compound of formula (III) are present in a 1:2 ratio, the compound of formula II preferably being in slight excess.

8. A pharmaceutical composition comprising
   a pharmaceutically effective amount of a bis(2-aminopyridine) compound of claim 1 or a physiologically acceptable addition salt thereof; and
   a pharmaceutically acceptable excipient or additive.

9. A pharmaceutical composition comprising
   a pharmaceutically effective dose of a bis(2-aminopyridine) compound of claim 2 or a physiologically acceptable addition salt thereof; and
   a pharmaceutically acceptable excipient or additive.

10. A pharmaceutical composition, comprising
    a pharmaceutically effective amount of a compound of formula (I) according to claim 2 or a physiologically acceptable addition salt thereof, in which $R_1$, $R_2$, $R_3$, and $R_4$ represent hydrogen atoms and Q represents a $C_6$–$C_{20}$ alkyl group; and
    a pharmaceutically acceptable excipient or additive.

11. A pharmaceutical composition for combating intraerythrocytic parasitoses comprising as active constituent an effective dose of at least one product of formula (I) according to claim 2, in which $R_1$, $R_2$, $R_3$, and $R_4$ represent hydrogen atoms and Q represents a $C_6$–$C_{20}$ alkyl group, with, in addition, appropriate excipients and additives.

12. A pharmaceutical composition for combating intraerythrocytic parasitoses, containing an active amount of at least one compound according to claim 1 or of an addition salt with an acid of such compound, with, in addition, appropriate excipients and additives.

13. A pharmaceutical composition for combating intraerythrocytic parasitoses, containing an active amount of at least one compound according to claim 2 or of an addition salt with an acid of such compound, with, in addition, appropriate excipients and additives.

* * * * *